United States Patent [19]
Schmider

[11] 3,937,576
[45] Feb. 10, 1976

[54] ILLUMINATION SYSTEM FOR AN ATOMIC ABSORPTION SPECTRAL PHOTOMETER

[75] Inventor: Paul Schmider, Munich-Oberfoehring, Germany

[73] Assignee: Beckman Instruments G.m.b.H., Munich, Germany

[22] Filed: Apr. 8, 1974

[21] Appl. No.: 458,973

[52] U.S. Cl. .................................. 356/74; 356/256
[51] Int. Cl.² .......................................... G01J 3/10
[58] Field of Search ...................... 356/74, 85-87, 356/96, 97, 256; 240/2 M

[56] References Cited
UNITED STATES PATENTS
3,825,344    7/1974    Bonne .................................. 356/85

OTHER PUBLICATIONS
Butler et al., Spectrochimica Acta, Vol. 21, July 1965, pp. 1207–1216.

Primary Examiner—Ronald L. Wibert
Assistant Examiner—F. L. Evans
Attorney, Agent, or Firm—R. J. Steinmeyer; P. R. Harder

[57] ABSTRACT

To compensate for the nonspecific absorption in an atomic absorption spectral photometer an auxiliary illuminating source is provided in addition to the principal illuminating source. The need for moving parts and mirrors is obviated by mounting the principal and auxiliary radiation sources in fixed positions along a common ray path. The auxiliary source is constructed so that it is optically transparent and mounted adjacent the optical input with the radiation concentrated in an emission center common to both sources coinciding with the emission center of the auxiliary source. The sources are pulsed so that they are energized alternately.

7 Claims, 1 Drawing Figure

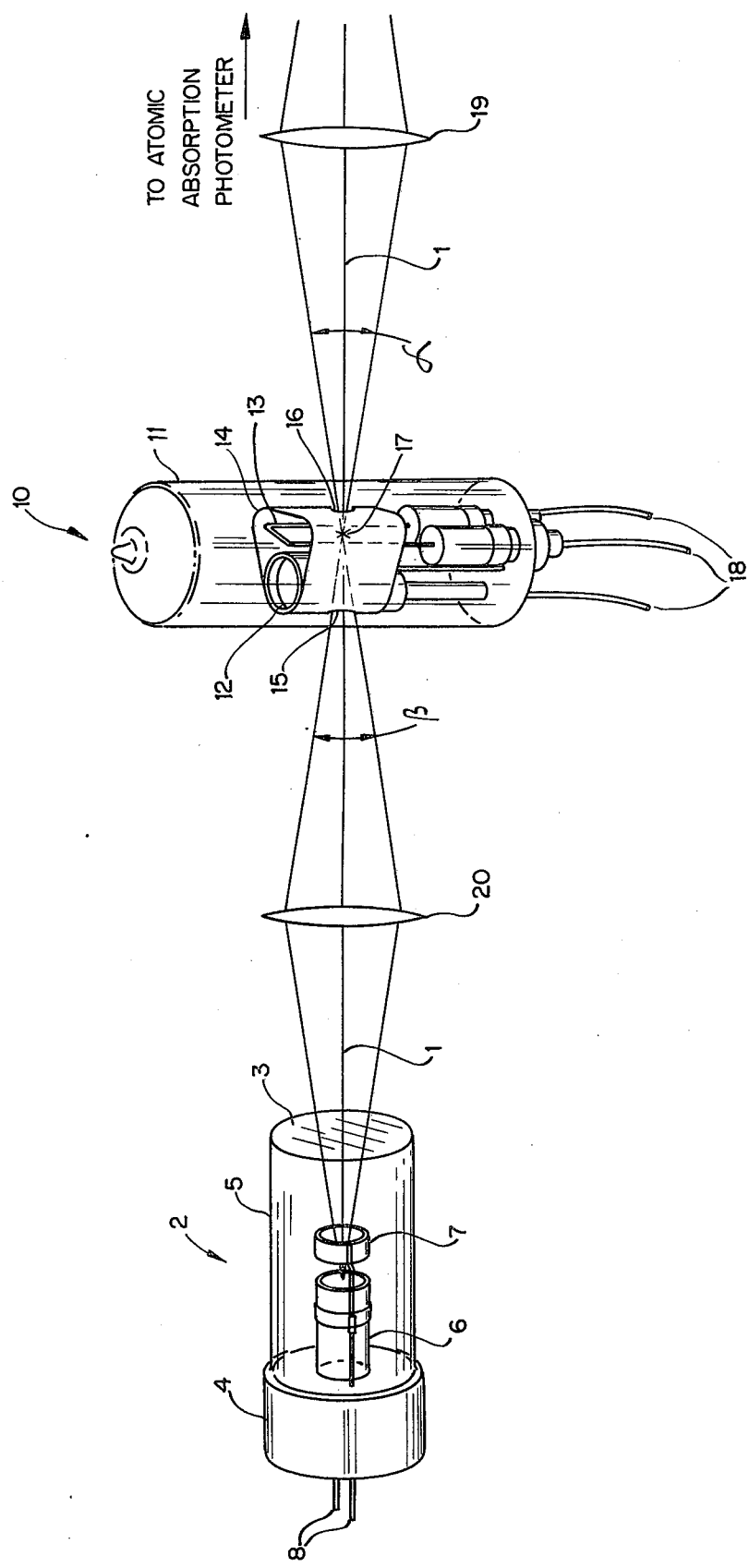

ILLUMINATION SYSTEM FOR AN ATOMIC ABSORPTION SPECTRAL PHOTOMETER

BACKGROUND OF THE INVENTION

Atomic absorption analysis represents a recently introduced system for the qualitative and quantitative determination of an element in a sample to be investigated on the basis of the specific atomic absorption of the element in question. The atomic absorption method is based on the physical discovery that free atoms contained in atomic vapor existing in the ground state, of an element which is to be detected, absorb only electromagnetic radiation which corresponds to the quantum energy uptake from the ground state to a higher energy condition.

Known atomic absorption spectral devices comprise as primary light sources hollow cathode lamps or other line emission sources which emit an atomic spectrum in a form of very narrow lines of the element or elements forming the cathode; furthermore, there is a device for converting the sample into atomic vapor and a wavelength separating device for selecting the resonance frequency light from the radiation emitted by the light source, as well as a detector device. With the help of optical projecting means the radiation emitted by the hollow cathode or the line emission source is passed through the atomic vapor and supplied via a wavelength separating device to the detector. The absorbed quantity of radiation measured at the resonance frequency line of the element in question is a measure of its concentration.

For converting the sample into an atomic vapor a proposal has already been made to atomize the sample to be analyzed either in a flame (flame atomic absorption method) or to heat the sample in any suitable manner thermally and to convert it into the vapor state (flameless atomic absorption method).

Furthermore it is also known that the specific absorption measured at the resonance frequency, and which forms the actual criterion for the quantitative determination of the element to be detected, has superimposed on it a nonspecific absorption, which is caused by effects such as absorption of the flame, molecular bands in the flame, absorption of the solvent, absorption of the matrix salt or dispersion by the solids present in concentrated solutions, so that the accuracy of the atomic absorption measurement is impaired.

In order to compensate for the nonspecific absorption, arrangements have already been proposed for atomic absorption spectral equipment, having the following parts: an auxiliary radiation source producing radiation within a wavelength range which comprises the resonance wavelength of the resonance radiation produced by the primary light source, and which is broad in comparison with the band width of this resonance radiation of the primary light source; a wavelength selection device which is arranged between the radiation sources and the radiation detector and serves for separating out a narrow wavelength band including the resonance wavelength of the hollow cathode lamp or line emission source; a device by means of which alternate pulses of the resonance radiation provided by the primary light source and of the radiation produced by the auxiliary radiation source are supplied along a reference and a sample ray path to the radiation detector; and circuit means responsive to the electric output signal of the radiation detector to produce an electrical signal having an amplitude which depends only upon the absorption due to the free atoms of the element to be analyzed and which is free of the interfering nonspecific absorption.

In the case of the prior art atomic absorption spectral equipment, as optical auxiliary means for reflecting the continuum radiation emitted by the auxiliary radiation source into the optical equipment systems, use is made of rotating mirror sectors or stationary semi-transparent mirrors, and the matching of the lamp energy of the primary light source and the auxiliary radiation source is carried out via iris diaphragms and/or gray wedges.

The use of rotating mirror sectors involves the disadvantages that on the one hand in the case of a rocking movement the optical identity of the ray paths of the primary and auxiliary ray sources in the absorption vessel is no longer guaranteed and on the other hand the measurement frequency is limited by the speed of rotation of the mirror sector arrangement whereby rapid compensation of the nonspecific absorption, as is required more particularly for the purposes of flameless absorption methods, is not possible.

The use of semi-transparent mirrors is disadvantageous in as far as their use involves substantial losses in energy and an offsetting of the ray which is dependent on the thickness, and, especially as to date it has not been possible to produce a dividing mirror in the UV-spectral range which is of interest for the absorption method.

SUMMARY OF THE INVENTION

The invention thus relates to an illumination system for an atomic absorption spectral photometer having an optical input, the system comprising a primary radiation source for producing a resonance radiation embracing the resonance wavelength of wavelengths of the element or elements to be detected, an auxiliary radiation source, which produces continuum radiation within a band or range of wavelengths which comprises the resonance wavelength or wavelengths of the primary resonance radiation and is broad in comparison with the band width of this resonance radiation of the primary source, for compensation of a nonspecific absorption in the absorption spectral device, and means for alternately supplying the optical system of the atomic spectral photometer with the primary resonance radiation and with the continuum auxiliary radiation.

The aim of the invention is the provision of an illumination system, intended for an atomic absorption spectral photometer, of the above-mentioned type, in the case of which the disadvantages of the prior art illumination arrangements with compensation for the non-specific absorption are avoided and which while having a simple construction without any moving parts makes possible a rapid automatic compensation for the non-specific absorption in such a manner that the absorption (at the resonance wavelength), which is of interest or significance as the actual measured quantity and which is based on the free atoms of the element to be analyzed, can be determined more accurately and more rapidly.

For this purpose in the case of an illumination system of the above-described type there is the provision in accordance with the invention that the primary radiation source and the auxiliary radiation are arranged in a fixed manner along a common ray path, in that the auxiliary radiation source is constructed so that it is optically transparent and is arranged adjacent to the optical input of the spectral photometer in that the radiation coming from the primary radiation source is supplied through the optically transparent auxiliary radiation source to the optical input of the spectral photometer and in that the primary and auxiliary radiation source are operated with alternate pulsing.

In accordance with the preferred embodiment of the invention it is possible to provide for the radiation leaving the primary radiation source to be concentrated by an optical system into an emission center common to both sources of radiation and the emission center common to both sources of radiation to coincide with the emission center of the auxiliary radiation source.

Preferably there is the provision that the energy matching of the radiation coming from the primary and the auxiliary radiation sources is carried out electrically.

The invention provides an illumination system for an atomic absorption spectral device which does not have any moving parts for reflecting the auxiliary radiation into the illumination ray path and there are also no stationary semi-transparent mirrors, which would bring about an undesired attenuation with the ray path or offsetting of the ray path. The two radiation sources can be arranged in a fixed manner along a common illumination radiation path, and in the case of a preferred embodiment of the invention the auxiliary radiation source can be arranged at the position of the common emission center and the radiation of the primary radiation source can be focused by a simple image forming system on to this common emission center within the auxiliary radiation source. In this respect it is possible to ensure in a simple manner that the radiation coming from the primary and auxiliary radiation sources is supplied using optically identical illumination apertures of the atomic absorption spectral device.

Since the alternating radiation from the primary and auxiliary sources is not carried out using mechanically moving parts but purely electrically using alternately pulsed operation of the two sources of radiation, substantially higher repetition frequencies of the alternating supply with the two types of radiation can be achieved as compared with the use of mechanical, rotating devices and thus more rapid compensation can be achieved as regards the undesired nonspecific absorption; for example in the case of a pulse frequency, which can readily be controlled, of 400 hz in the case of a measurement cycle of 2.5 msec the variations in indication caused by the nonspecific absorption in the case of the flameless atomic absorption method can be compensated for in a period of time of 5 msec.

In accordance with a convenient embodiment of the invention a hollow cathode lamp is used as a primary light source and use is made of an optically transparent deuterium lamp with a special construction as an auxiliary radiation source. It is possible to cause the auxiliary radiation source to be provided with a hollow-cylindrical anode with its axis perpendicular to the axis of the radiation path, a U-shaped cathode which is arranged along the ray path axis at some distance from the anode, and a screen electrode surrounding the anode and the cathode; and the anode and the screen electrode are provided with openings for the passage of radiation, the openings being adjacent to the passage positions of the optical ray path axis.

The alternating pulses, produced by the illumination system in accordance with the invention, of the primary radiation and/or the auxiliary radiation can be supplied in the optical system of the actual atom absorption spectral device in a conventional manner along a reference and a sample radiation path to the radiation detector, from whose output signal in an evaluation circuit the electrical output quantity is obtained, which is only dependent on the specific absorption depending on the free atoms of the element to be analyzed.

DRAWING

In what follows embodiments of the invention will be described with reference to the drawing, whose single FIGURE shows the principle and details of an embodiment of an illumination arrangement in accordance with the invention for an atomic absorption spectrophotometer.

DETAILED DESCRIPTION

In the drawing only the illumination system for an atomic absorption spectral photometer is shown; the atomic absorption spectrophotometer, which as such does not form a part of the subject matter of the invention, and can be constructed in a conventional manner, for example as a flame or preferably as a flameless atomic absorption spectrophotometer, is not shown in the drawing.

Reference numeral 1 denotes the axis of the radiation path of the illumination system, and along this axis the various components of the illumination system in accordance with the invention are arranged in a fixed manner and without any moving parts between them. In the specific embodiment shown the illumination radiation path 1 is made straight and linear; naturally, however, for example for reasons of compact construction or in order to save space it is possible to provide a construction of the arrangement in which the radiation path is deflected once or several times using radiation deflecting means which are conventional and suitable for the spectral range in question.

Reference numeral 2 denotes as general reference numeral a primary light source, whose emission comprises an intensive line spectrum of the element concerned which is to be detected in the sample with the atomic absorption analyzer. In the embodiment shown, the primary light source 2 is a conventional hollow cathode lamp, as available in various different constructions with emission spectra for various elements generally investigated with the help of atomic absorption spectroscopy. The hollow cathode lamp 2 has a glass vessel 5 with on the front side 3 a quartz window for the emergence of radiation and closed on the opposite face with a base 4 and a hollow cylindrical anode 7. Furthermore — as an essential part — there is a hollow cathode 6 which is mounted coaxially with the anode 7 which is placed in between them.

The hollow cathode 6 has the element or elements to be detected and ensures that the radiation emission emerging in the direction of the ray path through the end face 3 of the lamp comprises an intensive line spectrum with the resonance line or lines of the element or elements to be detected. The absorption of this resonance radiation by the element to be detected in the actual atomic absorption spectrometer itself is a criterium for the qualitative and quantitative analysis of the element in question in the sample to be investigated. The vessel of the hollow cathode lamp is filled with a protective gas or a mixture or protective gases, as for example helium, argon or neon, that is to say such gases whose natural emission lines do not disturb the atomic absorption measurement with respect to the element to be detected. From the physical point of view the hollow cathode lamp constitutes a gas discharge lamp, and in the case of commercially available construction the gas filling can have a pressure of approximately 1 Torr. The firing or ignition voltage of the lamp can be example amount of 450 V, its running voltage to about 200 V with a running current of for example 100 mA. Reference numeral 8 denotes the base pins for the (pulsed) supply of voltage.

The illumination system in accordance with the invention comprises as a further essential component an auxiliary radiation source denoted by general reference numeral 10, for compensation of the initially mentioned nonspecific absorption. The auxiliary radiation source is for this purpose so selected along conventional lines that the radiation produced by it lies within a wavelength range which comprises the resonance wavelength or lengths of the resonance radiation produced by the primary light source 2 and is comparatively broad or wide with respect to the band widths of this resonance radiation of the primary light source.

In accordance with the invention the auxiliary radiation source 10 is constructed as an optically transparent gas discharge lamp and is arranged in a stationary manner along the illumination ray path 1 at the position lying between the primary radiation source 2 and the input of the actual atomic absorption spectrometer and is constructed so as to be optically transparent in its ray producing system. More particularly, the auxiliary radiation source 10 comprises in the specific embodiment in question a radiation-transparent vessel 11 containing a radiation producing system having the following parts: A hollow cylindrical anode 12, which is arranged with its cylindrical axis, in the case of the specific embodiment, perpendicular to the ray path axis 1; a cathode 13 which in the case of the embodiment shown is in the form of a letter U, and a screen electrode 14 which surrounds the anode cylinder 12 and the cathode 13 and is connected electrically with the cathode. This screen electrode brings about a pinching of the gas discharge for obtaining an emission center (indicated by reference numeral 17) with a comparatively high illumination density. In accordance with the invention the screen electrode 14 is provided at mutually opposite positions along the ray path axis 1 with ray passage openings 15, 16; correspondingly, the anode cylinder 12 is provided, in alignment with the openings 15, 16 of the screen cylinder, with ray passage openings at diametrically opposite positions on the periphery along the axis 1 of the ray.

From the physical point of view the auxiliary radiation source 10 also constitutes a gas discharge lamp with a suitable filling gas, as for example deuterium, and can for example have a current consumption of 300 mA with a running voltage of 90 V.

Reference numeral 18 denotes supply leads for the operation and possibly the heater voltage. In a representative example the auxiliary radiation source provides a continuum radiation, suitable for compensation of the initially mentioned nonspecific absorption, in the range extending for approximately 190 to 400 millimicrons.

As mentioned the auxiliary radiation source 10 is arranged next to the actual atomic absorption spectrometer (on the right in terms of the drawing). Of the spectrometer in the drawing only the (quartz) input condensor 19 is indicated, which supplies the radiation leaving the emission center 17 within the aperture alpha to the absorption spectrometer. In accordance with the basic principle of the invention the auxiliary radiation source 10 is arranged in a stationary manner along the ray path 1 and the primary radiation source 2 is also arranged in a stationary manner on an extension of the ray path 1, and the emission center 17, formed essentially by the hollow cathode 6, of the primary radiation source 2 is imaged, via a quartz lens 20 at the emission center 17 of the auxiliary radiation source 10 in such a manner that the radiation coming from the hollow cathode 6 of the primary radiation source 2 is focused into the emission center 17 of the auxiliary radiation source 10 and from this position is passed onto the inlet condenser 19 of the following optical system of the atomic absorption spectral photometer. Preferably the aperture beta of the image of the hollow cathode 6 onto the emission center 17 is matched to suit the illumination aperture defined by the inlet condenser 19 and the distance of the emission center 17 of the auxiliary radiation source from the latter.

In accordance with the invention the primary and the auxiliary radiation sources 2 and 10 respectively are operated in a pulsed manner and the pulsed operation occurring with the same frequency of the two light sources is so electrically synchronized that the emission center 17 of the auxiliary radiation source sends out in an alternating manner light pulses of the primary radiation source 2 and of the auxiliary radiation source 10 which are supplied to the following optical system of the atomic absorption spectrophotometer. The energy matching between the auxiliary radiation source 10 and the primary radiation source 2 is carried out purely electrically avoiding the use of optical ray attenuators.

The invention thus provides an illumination system wherein alternating pulses of the resonance radiation supplied by the primary light source and/or the continuum radiation produced by the auxiliary source respectively are supplied to the optical system of the atomic absorption spectrometer from the emission center of the auxiliary radiation source arranged in a stationary manner along the ray path which is common to the primary and the auxiliary radiation source. In the spectrometer the radiation from both sources passes along a reference and sample path to a radiation detector. The detector produces, in a conventional manner, an electrical output signal having an amplitude dependent only on the specific absorption due to the free atoms of the element to be analyzed and is compensated for as regards undesired nonspecific absorption. This manner of operation is used in accordance with the invention with an optic illumination system which is simple in construction and makes do without any moving parts. The control of the pulse operation of the two radiation sources and of the energy emerging between the two radiation sources is carried out in a purely electrical or electronic manner.

The invention has been described above with reference to a preferred embodiment, which however can be modified in many different ways, more particularly as regards the details of the lamp construction. It is important for the basic principle of the invention that use is made of two radiation sources, arranged in a fixed manner along a common ray path, for the illumination system and the auxiliary radiation source is arranged closest to the optical inlet of the following atomic absorption spectrometer and in the ray producing system of the auxiliary radiation source there is an optically transparent part and the emission center of the primary radiation source arranged in a stationary manner along the same ray path is projected into the emission center of the auxiliary radiation source and the two radiation sources are operated in an alternate, pulsed manner and can be regulated electronically or electrically in their intensity.

What is claimed is:

1. An illumination system for an atomic absorption spectrophotometer having an optical input, the system comprising a primary radiation source for producing resonant radiation encompassing the resonant wavelength or wavelengths of the element or elements to be detected, an auxiliary radiation source which produces a continuum of radiation within a wavelength range which includes the resonance wavelength or wavelengths of the primary resonance radiation and is broad in comparison with the band width of the resonance radiation of the primary source for compensation of a nonspecific absorption in the absorption spectral photometer and means for causing the radiation from the two sources to enter the optical input of the spectral photometer alternately, wherein the improvement comprises:
mounting the primary radiation source and the auxiliary radiation source in a common path, said auxiliary source having an area therethrough transparent to the radiation of the primary source and being mounted between said primary source and the optical input of the absorption spectral photometer.

2. The illumination system defined in claim 1 including an optical system for focusing the radiation from the primary radiation source in an emission center common to both radiation sources.

3. The system defined in claim 2 wherein the emission center common to the two radiation sources coincides with the emission center of the auxiliary radiation source.

4. The system defined in claim 3 wherein the primary radiation source has an aperture beta and the optical input of the atomic absorption spectrophotometer has an aperture alpha matching the aperture beta.

5. The system defined in claim 1 wherein electrical means are provided for alternately pulsing the radiation sources.

6. The system defined in claim 1 wherein the auxiliary radiation source comprises a gas discharge lamp having ray producing elements with openings arranged along the optical axis of the primary radiation source.

7. An illumination system for an atomic absorption spectrophotometer having an optical input, the system comprising a primary radiation source for producing resonance radiation encompassing the resonance wavelength or wavelengths of the element or elements to be detected, an auxiliary radiation source which produces a continuum of radiation within a wavelength range which includes the resonance wavelength or wavelengths of the primary resonance radiation and is broad in comparison with the band width of the resonance radiation of the primary source for compensation of a nonspecific absorption in the absorption spectral photometer and means for causing the radiations from the two sources to enter the optical input of the spectral photometer alternately, wherein the improvement comprises:
mounting the primary radiation source and the auxiliary radiation source on a common optical path;
said auxiliary source being mounted between said primary source and the optical input to the spectral photometer;
said auxiliary radiation source comprising a hollow cylindrical anode having an axis perpendicular to said optical path, a cathode of U-shaped form and a screen electrode which surrounds the anode and the cathode, said anode and said screen electrode having apertures therein along said common optical path whereby radiation from said primary source may pass through said auxiliary radiation source.

* * * * *